United States Patent
Scheidel et al.

(10) Patent No.: US 7,781,608 B2
(45) Date of Patent: *Aug. 24, 2010

(54) PRODUCTION OF 3-PENTENENITRILE FROM 1,3-BUTADIENE

(75) Inventors: Jens Scheidel, Hirschberg (DE); Tim Jungkamp, Kapellen (BE); Michael Bartsch, Neustadt (DE); Gerd Haderlein, Grünstadt (DE); Robert Baumann, Mannheim (DE); Hermann Luyken, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 1037 days.

This patent is subject to a terminal disclaimer.

(21) Appl. No.: 10/585,590

(22) PCT Filed: Jan. 27, 2005

(86) PCT No.: PCT/EP2005/000784

§ 371 (c)(1),
(2), (4) Date: Jul. 11, 2006

(87) PCT Pub. No.: WO2005/073175

PCT Pub. Date: Aug. 11, 2005

(65) Prior Publication Data

US 2009/0187039 A1    Jul. 23, 2009

(30) Foreign Application Priority Data

Jan. 29, 2004    (DE)  .................... 10 2004 004 724

(51) Int. Cl.
*C07C 263/00* (2006.01)
(52) U.S. Cl. ...................................... 558/335
(58) Field of Classification Search .................. 558/335
See application file for complete search history.

(56) References Cited

U.S. PATENT DOCUMENTS

| 6,197,992 | B1 | 3/2001 | Fischer et al. | |
| 7,439,381 | B2 * | 10/2008 | Jungkamp et al. | ........... 558/322 |
| 7,538,240 | B2 * | 5/2009 | Jungkamp et al. | ........... 558/308 |
| 7,541,486 | B2 * | 6/2009 | Scheidel et al. | ............. 558/465 |

FOREIGN PATENT DOCUMENTS

WO        WO-98/27054       6/1998

* cited by examiner

*Primary Examiner*—Rei-tsang Shiao
(74) *Attorney, Agent, or Firm*—Connolly Bove Lodge & Hutz

(57) ABSTRACT

A process is described for preparing 3-pentenenitrile by hydrocyanating 1,3-butadiene, wherein 1,3-butadiene is reacted with hydrogen cyanide in the presence of at least one catalyst and the stream resulting therefrom is purified distillatively, the bottom temperature during the distillation not exceeding 140° C.

10 Claims, 1 Drawing Sheet

PRODUCTION OF 3-PENTENENITRILE FROM 1,3-BUTADIENE

RELATED APPLICATIONS

This application is a national stage application (under 35 U.S.C. 371) of PCT/EP2005/000784 filed Jan. 27, 2005, which claims benefit to German application 10 2004 004 724.3 filed Jan. 29, 2004.

The present invention relates to a process for preparing 3-pentenenitrile.

Adiponitrile is an important starting material in nylon production and is obtained by double hydrocyanation of 1,3-butadiene. In a first hydrocyanation, 1,3-butadiene is hydrocyanated to 3-pentenenitrile, and the by-products obtained are mainly 2-methyl-3-butenenitrile, 4-pentenenitrile, 2-pentenenitriles, 2-methyl-2-butenenitriles, $C_9$ nitriles and methylglutaronitrile. In a second, subsequent hydrocyanation, 3-pentenenitrile is reacted with hydrogen cyanide to give adiponitrile. Both hydrocyanations are catalyzed by nickel (0)-phosphorus complexes.

For the second hydrocyanation, it is essential that the 3-pentenenitrile used is free of 2-methyl-3-butenenitrile, since 2-methyl-3-butenenitrile is otherwise hydrocyanated to the undesired by-product methylglutaronitrile.

A general review of nickel-catalyzed olefin hydrocyanation is given in Tolman et al., Adv. Cat. 33, 1-46 (1985).

The hydrocyanation of 1,3-butadiene using a nickel catalyst of the formula $Ni[P(OR)_3]_4$ is described in U.S. Pat. No. 3,496,215. A disadvantage of this process is that no suitable technique for fully recovering the 1,3-butadiene or the catalyst is specified.

U.S. Pat. No. 5,693,843, U.S. Pat. No. 5,696,280, U.S. Pat. No. 5,821,378 and U.S. Pat. No. 5,981,772 describe hydrocyanations of 1,3-butadiene with multidentate phosphorus ligands, although no suitable procedure for the recovery of the catalyst components is shown in the individual embodiments.

The performance of the hydrocyanation in one or more reactors and their connection is described in U.S. Pat. No. 4,810,815, and the possibility is mentioned of continuous operation of stirred tanks or batteries of stirred tanks, but only a semibatch mode is described in detail in examples, from which it cannot be directly discerned by those skilled in the art under which conditions the method has to proceed in continuous stirred tanks.

A process for removing organic phosphorus compounds and their metal complexes from organic nitriles in the hydrocyanation of olefins is described in U.S. Pat. No. 3,773,809. The removal is effected by contacting the product with a cycloparaffin or a paraffinic hydrocarbon. This forms a liquid multiphasic system. This method of removing and recovering catalyst components by extraction cannot be applied in the hydrocyanation of 1,3-butadiene owing to the concentration of dinitriles in the reaction product being too low.

Furthermore, it is crucial for an integrated process for preparing 3-pentenenitrile in which both the 1,3-butadiene and the hydrocyanation catalyst stream are recycled that the 1,3-butadiene used in a molar excess relative to hydrogen cyanide is recycled efficiently.

It is thus an object of the present invention to provide an integrated process for preparing 3-pentenenitrile by hydrocyanating 1,3-butadiene, in which the process yield based on 1,3-butadiene is very high, even though the cis-2-butene which is present in commercial butadiene but is unreactive in the hydrocyanation accumulates in the butadiene cycle and therefore has to be discharged, which is associated with a forced discharge of 1,3-butadiene. The process according to the invention accordingly features a small loss of 1,3-butadiene owing to discharge.

This object is achieved by a process for preparing 3-pentenenitrile by hydrocyanating 1,3-butadiene, characterized by the following process steps:

(a) reacting 1,3-butadiene which comprises cis-2-butene with hydrogen cyanide over at least one catalyst to obtain a stream 1 which comprises 3-pentenenitrile, 2-methyl-3-butenenitrile, the at least one catalyst, 1,3-butadiene and residues of hydrogen cyanide which has yet to be converted, (b) distilling stream 1 in a distillation apparatus K1 to obtain a stream 2 as the top product which comprises the predominant portion of the 1,3-butadiene from stream 1, and a stream 3 as the bottom product which comprises 3-pentenenitrile, the at least one catalyst, 2-methyl-3-butenenitrile and the remaining portion of the 1,3-butadiene from stream 1 which has not been removed in stream 2, (c) distilling stream 3 in a distillation apparatus K2 to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst, (d) distilling stream 5 to obtain a stream 7 as the top product which comprises 2-methyl-3-butenenitrile, and a stream 8 as the bottom product which comprises 3-pentenenitrile the distillation apparatus K1 used in process step (b) comprising at least one distillation column having a stripping section and/or the distillation apparatus K2 used in process step (c) having distillative separation stages between the feed of stream 3 and the draw of stream 5 being disposed lower in the distillation apparatus K2 than the feed of stream 3.

The proportion of the 1,3-butadiene from stream 1 which is referred to above as the predominant portion of the 1,3-butadiene from stream 1 and is removed with stream 2 refers to a proportion of preferably more than 50%, more preferably more than 60%, in particular more than 70%, of the 1,3-butadiene which is present in stream 1. The correspondingly remaining 1,3-butadiene from stream 1 is transferred into process step (c) via stream 3.

DETAILED DESCRIPTION

Figure 1:
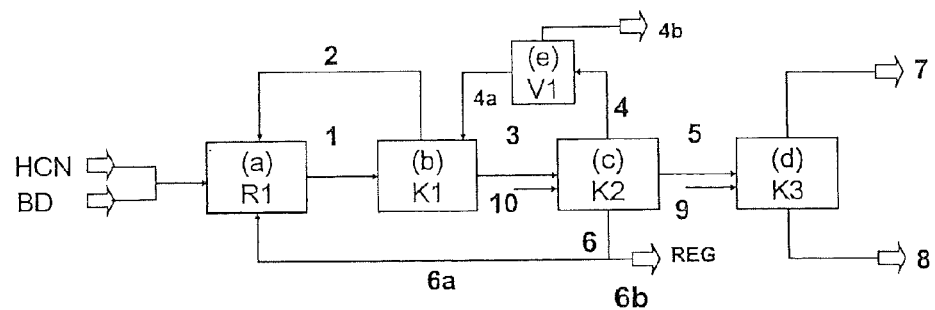
FIGS. 1-3 schematically illustrate practices of this invention.

Process step (a) comprises the reaction of 1,3-butadiene with hydrogen cyanide over at least one catalyst. The catalysts used are homogeneously dissolved nickel(0) catalyst complexes.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

$P(X^1R^1)(X^2R^2)(X^3R^3)$  (I).</p>"

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1R^2R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified in this description.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula I a

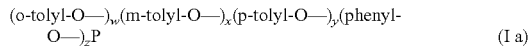

(I a)

where w, x, y, z are each a natural number and the following definitions apply: w+x+y+z=3 and w, z≦2.

Such compounds I a are, for example, (p-tolyl-O—)(phenyl-O—)$_2$P,
(m-tolyl-O—)(phenyl-O—)$_2$P, (o-tolyl-O—)(phenyl-O—)$_2$P, (p-tolyl-O—)$_2$(phenyl-O—)P,
(m-tolyl-O—)$_2$(phenyl-O—)P, (o-tolyl-O—)$_2$(phenyl-O—)P,
(m-tolyl-O—)(p-tolyl-O—)(phenyl-O—)P, (o-tolyl-O—)(p-tolyl-O—)(phenyl-O—)P,
(o-tolyl-O—)(m-tolyl-O—)(phenyl-O—)P, (p-tolyl-O—)$_3$P, (m-tolyl-O—)(p-tolyl-O—)$_2$P,
(o-tolyl-O—)(p-tolyl-O—)$_2$P, (m-tolyl-O—)$_2$(p-tolyl-O—)P, (o-tolyl-O—)$_2$(p-tolyl-O—)P,
(o-tolyl-O—)(m-tolyl-O—)(p-tolyl-O—)P, (m-tolyl-O—)$_3$P, (o-tolyl-O—)(m-tolyl-O—)$_2$P,
(o-tolyl-O—)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

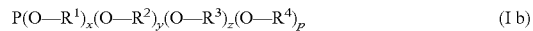

(I b)

where
$R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that x+y+z+p=3.

Preferred phosphites of the formula I b can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |

-continued

| x | y | z | p |
|---|---|---|---|
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

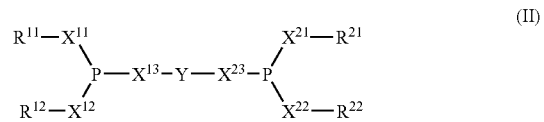

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals too may each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003, which has an earlier priority date but had not been published at the priority date of the present application.

The compounds I, I a, I b and II described and their preparation are known per se. Phosphorus ligands used may also be mixtures comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

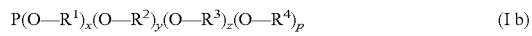  (I b)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that x+y+z+p=3; and mixtures thereof.

Process step (a) of the process according to the invention may be carried out in any suitable apparatus known to those skilled in the art. Useful apparatus for the reaction is customary apparatus, as described, for example, in: Kirk-Othmer, Encyclopedia of Chemical Technology, 4th Ed. Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. It has been found that particularly advantageous batteries of reactors having backmixing characteristics are those which are operated in cross-flow mode with regard to the metering of hydrogen cyanide.

The hydrocyanation may be carried out in the presence or in the absence of a solvent. When a solvent is used, the solvent should be liquid and inert toward the unsaturated compounds and the at least one catalyst at the given reaction temperature and the given reaction pressure. In general, the solvents used are hydrocarbons, for example benzene or xylene, or nitriles, for example acetonitrile or benzonitrile. However, preference is given to using a ligand as the solvent.

The reaction may be carried out in batch mode, continuously or in semibatchwise operation.

The hydrocyanation reaction may be carried out by charging the apparatus with all reactants. However, it is preferred when the apparatus is filled with the catalyst, the unsaturated organic compound and, if appropriate, the solvent. The gaseous hydrogen cyanide preferably floats over the surface of the reaction mixture or is passed through the reaction mixture. A further procedure for charging the apparatus is the filling of the apparatus with the catalyst, hydrogen cyanide and, if appropriate, the solvent, and slowly metering the unsaturated compound into the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

Preference is given to carrying out the hydrocyanation continuously in one or more stirred process steps. When a multitude of process steps is used, preference is given to the process steps being connected in series. In this case, the product is transferred from one process step directly into the next process step. The hydrogen cyanide may be fed directly into the first process step or between the individual process steps.

When the process according to the invention is carried out in semibatchwise operation, preference is given to initially charging the catalyst components and 1,3-butadiene in the reactor, while hydrogen cyanide is metered into the reaction mixture over the reaction time.

The reaction is preferably carried out at absolute pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, in each case per reactor.

In one embodiment, the reaction may be performed in the liquid phase in the presence of a gas phase and, if appropriate, of a solid suspended phase. The starting materials, hydrogen cyanide and 1,3-butadiene, may each be metered in in liquid or gaseous form.

In a further embodiment, the reaction may be carried out in liquid phase, in which case the pressure in the reactor is such that all feedstocks such as 1,3-butadiene, hydrogen cyanide and the at least one catalyst are metered in in liquid form and are in the liquid phase in the reaction mixture. A solid suspended phase may be present in the reaction mixture and may also be metered in together with the at least one catalyst, for example consisting of degradation products of the catalyst system comprising nickel(II) compounds inter alia.

In process step (a), a stream 1 is obtained which comprises 3-pentenenitrile, 2-methyl-3-butenenitrile, the at least one catalyst and unconverted 1,3-butadiene, and also residues of unconverted hydrogen cyanide. This stream 1 preferably has the following composition: from 1 to 80% by weight, more preferably from 5 to 50% by weight, of the at least one catalyst, from 0.1 to 50% by weight, more preferably from 1 to 25% by weight, of 1,3-butadiene, from 1 to 80% by weight, more preferably from 10 to 50% by weight, of pentenenitriles comprising trans-3-pentenenitrile, 2-methyl-3-butenenitrile and also further pentenenitrile isomers, and from 0.1 ppm by weight to 10% by weight, more preferably from 10 ppm by weight to 1% by weight, of hydrogen cyanide, based in each case on the overall composition of stream 1.

Stream 1 which comprises 3-pentenenitrile, 2-methyl-3-butenenitrile, the at least one catalyst and unconverted 1,3-butadiene is subsequently transferred into a distillation apparatus K1 in process step (b). In this distillation apparatus, stream 1 is distilled to obtain a high-1,3-butadiene stream 2 as the top product and a low-1,3-butadiene stream 3 as the bottom product which comprises 3-pentenenitrile, the at least one catalyst and 2-methyl-3-butenenitrile.

Process step (b) of the process according to the invention may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in a single apparatus.

In a preferred embodiment of the process according to the invention, column internals having structured packing are present in the distillation apparatus and preferably generate between 2 and 60, more preferably between 3 and 40, in particular between 4 and 20, separation stages.

In a particularly preferred embodiment of the process according to the invention, the at least one evaporator stage associated with the distillation apparatus of process step (b) is designed in such a way that the material to be evaporated is subject to very little thermal damage, as achieved, for example, by falling-film evaporators, multiphase helical tube evaporators, thin-film evaporators or short-path evaporators by short contact times of the material on the evaporator surface and very low temperatures of the evaporator surfaces.

In a preferred embodiment of the process according to the invention, the distillation apparatus of process step (b) is operated with a divided column bottom, in which case a circulation stream which is generally several times larger than stream 3 is conducted from a first column bottom of the distillation column in question to the evaporator, but the liquid effluent stream from the evaporator is not returned directly to the first column bottom and instead collected in a second column bottom which is separate from the first column bottom, stream 3 is obtained from the second column bottom and the remaining excess of evaporator circulation stream is allowed to overflow into the first column bottom to obtain, as stream 3 from the second column bottom, a mixture which is depleted in low boilers compared to the evaporator circulation stream drawn off from the first column bottom. The evaporator used is preferably a falling-film evaporator.

In a further preferred embodiment of the process according to the invention, the distillation is carried out at average residence times of the liquid phase in the bottom region of the one or more distillation apparatuses in process step (b) of together less than 10 hours, more preferably less than 5 hours, in particular less than 1 hour.

In a further preferred embodiment of the process according to the invention, the condensation at the top of the distillation apparatus is carried out in such a way that a substream of the top effluent is flushed back into the condenser.

In a further preferred embodiment of the process according to the invention, the distillation may be performed with a direct condenser, so that the condensation is carried out in a column section which is preferably equipped with a structured column packing, a collecting cup below this packing, a liquid draw from the collecting cup, a pumped circulation system, attached to the liquid draw, having a pump and heat exchanger, and also at least one apparatus for applying the liquid stream pumped in circulation to the packing above the collecting cup.

The distillation apparatus K1 used in process step (b) comprises a distillation column having stripping section, and the distillation column preferably has from 2 to 60, preferably from 3 to 40, in particular from 4 to 20, theoretical plates. In order to achieve a very high process yield with respect to 1,3-butadiene in spite of the only partial conversion in step (a), preference is given to recycling the high-1,3-butadiene stream 2 into process step (a). The recycling of stream 2 into process step (a) may, if appropriate, also only be partial.

In a further embodiment, in the distillation of step (b), the 1,3-butadiene additionally required for the reaction in process step (a) may be added to the top region of the column or to stream 2.

In a further embodiment, the 1,3-butadiene added comprises a stabilizer, such as tert-butylpyrocatechol or 2,6-di-tert-butyl-para-cresol, according to the description in "Ullmann's Encyclopedia Of Industrial Chemistry, 6th Edition, 2000 Electronic Release, chapter "Butadiene—6. Stabilization, Storage and Transportation".

In a particularly preferred embodiment of the process according to the invention, the 1,3-butadiene either used directly in process step (a) or added to process step (b) and transferred via stream 2 to step (a) is freed of water and, where present, the stabilizer by contacting with molecular sieve having a pore size less than 10 angstrom or by contacting with alumina.

In a further particularly preferred embodiment, the 1,3-butadiene used in the process, i.e. that used directly in process step (a) or the 1,3-butadiene fed into stream 2, does not have any stabilizer, in which case suitable selection of the pressure conditions keeps the condensation temperatures in the top region of the distillation unit of process step (b) less than 293 K in order to prevent polymerization of 1,3-butadiene, especially in order to restrict the growth of popcorn polymer nuclei.

Commercial 1,3-butadiene comprises cis-2-butene in significant amounts.

1-Butene is formed as a by-product of the hydrocyanation of 1,3-butadiene using nickel(0) catalysts.

Both cis-2-butene and 1-butene accumulate in the cycle of the 1,3-butadiene of the process according to the invention depending on how good the efficiency of the recycling is. The more completely 1,3-butadiene is recycled, the earlier the accumulations become noticeable.

Stream 2 is thus preferably generated in such a way that it contains less than 50% by weight, more preferably less than 25% by weight, in particular less than 15% by weight, and preferably more than 1% by weight, more preferably more than 2.5% by weight, in particular more than 5% by weight, in total of trans-2-butene, cis-2-butene and 1-butene. The remainder is substantially 1,3-butadiene.

One means of restricting the accumulation of the butene isomers to the desired value is to discharge a substream from the stream 2 recycled into process step (a). This is in some cases associated with losses of 1,3-butadiene, since, on the one hand, the cis-2-butene content in the cycle stream 2 must not rise too high, but, on the other hand, 1,3-butadiene is inevitably always discharged in this discharge. Stream 2 is preferably withdrawn in gaseous form.

A further means for removing cis-2-butene from the butadiene cycle is, in accordance with the invention, to operate the distillation apparatus K1 in such a way that, below the feed of stream 1, separating stages are active and permit an accumulation of cis-2-butene relative to 1,3-butadiene in stream 3. Instead of a discharge from stream 2, there is then a discharge in process step (c) in the form of stream 4b which is generated from stream 3 as described below in a preferred embodiment.

The discharges are preferably in gaseous form.

The absolute pressure in process step (b) is preferably from 0.001 to 100 bar, more preferably from 0.01 to 10 bar, in particular from 0.5 to 5 bar. The distillation is carried out in such a way that the temperature in the bottom of the distillation apparatus is preferably from 30 to 140° C., more preferably from 50 to 130° C., in particular from 60 to 120° C. The distillation is carried out in such a way that the condensation temperature at the top of the distillation apparatus is preferably from −50 to 140° C., more preferably from −15 to 60° C., in particular from 5 to 45° C. In a particularly preferred embodiment of the process according to the invention, the aforementioned temperature ranges are maintained both at the top and in the bottom of the distillation apparatus.

The reflux ratio at the top of the distillation apparatus is preferably adjusted in such a way that stream 2 contains from 1 to 1000 ppm, more preferably from 5 to 500 ppm, in particular from 10 to 200 ppm, of 2 methyl-3-butenenitrile.

In process step (b), a high-1,3-butadiene stream 2 is obtained as the top product and a low-1,3-butadiene stream 3 as the bottom product. The designation of the streams as high-1,3-butadiene or low-1,3-butadiene is based on the content of 1,3-butadiene of the stream 1 used in process step (b).

In a preferred embodiment of the process according to the invention, the high-1,3-butadiene stream 2 contains a total of from 50 to 100% by weight, more preferably from 80 to 100% by weight, in particular from 85 to 99% by weight, of 1,3-butadiene and butene isomers, and also a total of from 0 to 50% by weight, more preferably from 0 to 20% by weight, in particular from 10 ppm by weight to 1% by weight, of pentenenitrile isomers, of which substantially 2-methyl-3-butenenitrile and trans-3-pentenenitrile are present in stream 2.

In a preferred embodiment of the process according to the invention, the low-1,3-butadiene stream 3 contains a total of from 0 to 50% by weight, more preferably from 1 to 30% by weight, in particular from 2 to 20% by weight, of 1,3-butadiene and butene isomers, based in each case on the overall-composition of stream 3. In a particularly preferred embodiment of the process according to the invention, the aforementioned specifications of 1,3-butadiene are achieved both in stream 2 and in stream 3.

The stream 2 which is obtained in process step (b) and comprises 1,3-butadiene is, if appropriate before it has been recycled into process (a), preferably condensed. This may be effected, for example, by indirect heat removal using a condenser.

Alternatively, it is also possible that, in process step (b) in the rectifying section of the distillation column, a stream is obtained in the boiling state at a side draw of the distillation apparatus K1, condensed on a condenser by indirect heat removal to obtain a cooled stream and recycled to the top of the distillation apparatus K1, and a stream 2' is drawn off from the stream before or after the condensation and the stream 2' is recycled into process step (a) instead of stream 2.

It is preferred that no stabilizer is added to stream 2'. The resulting stream 2' may be recycled into process step (a) for the purpose of its economic use.

Before its use, stream 2' is to be regarded as equivalent to stream 2. Statements on stream 2 are therefore equally valid for stream 2' and vice versa.

The low-1,3-butadiene stream 3 stemming from process step (b) and comprising 3-pentenenitrile, the at least one catalyst and 2-methyl-3-butenenitrile is subsequently transferred to a distillation apparatus in process step (c). In this distillation apparatus, stream 3 is distilled to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst.

Process step (c) of the process according to the invention may be carried out in any suitable apparatus known to those skilled in the art. Suitable apparatus for this distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in one apparatus.

In a particularly preferred embodiment, the distillation apparatus selected in process step (c) is at least one distillation column which has a stripping section, more preferably only one distillation column which has only one stripping section.

The distillation apparatus is preferably equipped with a structured packing which generates from 2 to 50, more preferably from 3 to 40, in particular from 4 to 30, theoretical plates.

In a particularly preferred embodiment of the process according to the invention, the at least one evaporator stages associated with the distillation apparatus of process step (c) are designed in such a way that the material to be evaporated is subject to very little thermal damage, as achieved, for example, by falling-film evaporators, multiphase helical tube evaporators, thin-film evaporators or short-path evaporators by short contact times of the material on the evaporator surface and very low temperatures of the evaporator surfaces.

In a further preferred embodiment of the process according to the invention, the distillation is carried out at average residence times of the liquid phase in the bottom region of the distillation apparatus in process step (c) of together less than 10 hours, more preferably less than 5 hours, in particular less than 1 hour.

In a particularly preferred embodiment of the process according to the invention, the distillation is carried out at average residence times of the liquid phase in the bottom region of the distillation apparatus in process steps (b) and (c) of together less than 10 hours, more preferably less than 5 hours, in particular less than 1 hour.

The absolute pressure in process step (c) is preferably from 0.001 to 10 bar, more preferably from 0.010 to 1 bar, in particular from 0.020 to 0.5 bar. The distillation is carried out in such a way that the temperature in the bottom of the distillation apparatus is preferably from 30 to 140° C., more preferably from 40 to 130° C., in particular from 50 to 120° C. The distillation is carried out in such a way that the condensation temperature at the top of the distillation apparatus is preferably from −20 to 140° C., more preferably from −10 to 80° C., in particular from −5 to 60° C. In a particularly preferred embodiment of the process according to the invention, the aforementioned temperature ranges are maintained both at the top and in the bottom of the distillation apparatus.

In the distillation of process step (c), a stream 4 is obtained as the top product. This stream 4 preferably contains a total of from 50 to 100% by weight, more preferably from 80 to 100% by weight, in particular from 90 to 99.9% by weight, of 1,3-butadiene and butene isomers, and also a total of from 0 to 50% by weight, more preferably from 0 to 20% by weight, in particular from 10 ppm by weight to 10% by weight, of pentenenitrile isomers, of which substantially 2-methyl-3-butenenitrile and trans-3-pentenenitrile are present in stream 4.

In a preferred embodiment of the process according to the invention, stream 4 is obtained in gaseous form in at least one condenser at the top of the distillation apparatus, and pentenenitrile components from the vapor stream of the distillation apparatus of process step (c) are at least partly condensed out in the at least one condenser in the abovementioned range of condensation conditions such as pressure and temperature, and recycled into the column at least partly in liquid form as a stream comprising pentenenitriles and also 1,3-butadiene and butene isomers.

In order to increase the process yield of 1,3-butadiene used in the process according to the invention, preference is given to recycling stream 4 directly or indirectly into process step (a). Indirect recycling of stream 4 into process step (a) means that stream 4 is recycled initially into the distillation apparatus K1 of process step (b) and then into process step (a) via stream 2.

Particular preference is given to the indirect recycling of stream 4, in which case the pentenenitrile components which may be present in stream 4 depending on the distillation conditions are preferably removed from stream 4 by recycling stream 4 into the distillation apparatus of process step (b) and ultimately only the 1,3-butadiene and butene isomers content of stream 4 is recycled via stream 2 into step (a). The recycling of stream 4 may in some cases also only be partial. Before it is recycled, stream 4 may additionally be subjected to one or more operations for the purposes of the process, for example a compression to a higher pressure.

In one embodiment of the process according to the invention, stream 4 is partly recycled (stream 4a) without or after delay into the distillation apparatus K1 of process step (b) and a substream 4b is withdrawn from stream 4 in liquid or gaseous form for discharge. This is particularly advantageous because stream 4 comprises a higher proportion of butene isomers and thus less butadiene than in stream 2, the forced discharge of butadiene thus becomes lower and the process yield thus becomes higher, and the content of butene isomers can be kept at the level described as advantageous above.

The content of trans-2-butene, cis-2-butene and 1-butene in total in the recycled stream 4 or 4a is preferably more than 2% by weight, more preferably more than 10% by weight, in particular more than 15% by weight, and preferably less than 80% by weight, more preferably less than 70% by weight, in particular less than 50% by weight.

Before stream-4 is obtained, nitrile-containing compounds are preferably depleted by multistage condensations of the vapor stream of the distillation apparatus K2.

The stream 4 or 4a which is obtained at the distillation apparatus K2 in process step (c) is preferably drawn off in vaporous form and compressed with a compression apparatus V1 and with a pressure increase. This provides a compressed stream 4 or 4a.

This compressed stream 4 or 4a is preferably liquefied by condensation. This forms a liquefied stream 4 or 4a.

The thus compressed and/or liquefied stream 4 is subsequently recycled into the distillation apparatus K1 of process step (b).

In a particularly preferred embodiment, stream 4 or 4a is introduced into the reflux section of the divided column bottom of the distillation apparatus in process step (b).

Before its use, stream 4a is to be regarded as equivalent to stream 4. Statements on stream 4 are therefore equally valid for stream 4a and vice versa.

In process step (c), in addition to stream 4, a further stream 5 is obtained which is recovered at a side draw of the column. This stream 5 comprises 3-pentenenitrile and 2-methyl-3-butenenitrile, in addition to other pentenenitrile isomers and residual constituents of 1,3-butadiene and butene isomers. The proportion of 3-pentenenitrile and 2-methyl-3-butenenitrile in stream 5 is a total of preferably from 80 to 100% by weight, more preferably from 85 to 99.998% by weight, in particular from 90 to 99.9% by weight, based in each case on stream 5. The proportion of 1,3-butadiene and butene isomers in stream 5 is preferably from 0 to 20% by weight, more preferably from 10 ppm by weight to 5% by weight, in particular from 50 ppm by weight to 2% by weight, based in each case on stream 5. Stream 5 is preferably withdrawn in vaporous form.

The side draw of the distillation apparatus is preferably disposed below the feed point of stream 3, more preferably in a position corresponding to from 1 to 20, in particular from 2 to 10, distillative separation stages below the feed point of stream 3.

The bottom product obtained in process step (c) is a stream 6 which comprises the at least one catalyst, and also trans-3-pentenenitrile and 2-methyl-3-butenenitrile. The proportion of pentenenitrile isomers in stream 6 is a total of preferably from 0.1 to 80% by weight, more preferably from 5 to 50% by weight, in particular from 10 to 40% by weight, based in each case on stream 6.

In addition, particular preference is given to at least partly recycling stream 6 into process step (a) of the hydrocyanation. It is possible that the recycled catalyst is subjected partly to a regeneration, for example as described in the German patent application DE . . . with the title "Use of azeotropically dried nickel(II) halide" to BASF AG (B03/0484).

In a preferred embodiment of the process according to the invention, the content of 2-methyl-3-butenenitrile in this recycled stream 6 is less than 10% by weight, more preferably less than 5% by weight, in particular less than 1% by weight. This is achieved by providing enough distillative separation stages between the draw point for stream 5 and the draw point for stream 6.

In a preferred embodiment, the thermal stress on the catalyst can be kept low by the bottom temperature not exceeding 140° C., which can be ensured by suitable pressure conditions.

In addition, it is also possible to fully or partly use stream 6 from process step (c) as a catalyst stream for other hydrocyanations, for example for hydrocyanating 3-pentenenitrile. When catalyst stream 6 is used for hydrocyanating 3-pentenenitrile, it is also preferred that the content of 2-methyl-3-butenenitrile in this catalyst stream 6 is very low and does not exceed the aforementioned values.

In a further preferred embodiment, a fresh catalyst stream is conducted into the distillation apparatus of process step (c) in order to be able to control the pentenenitrile content of the entire catalyst stream to process step (a) within the above-mentioned limits.

In a further preferred embodiment of the process according to the invention, the amount of catalyst discharge and thus the amount of fresh catalyst needed for supplementation is adjusted such that the content of methylglutaronitrile in the catalyst circulation is not above 50% by weight, more preferably not above 20% by weight, in particular not above 10% by weight, based in each case on the catalyst circulation, in order to have the particular catalyst stream discharged present in a regeneration with very minor inhibiting effects of methylglutaronitrile to the uptake of nickel(0).

In a further preferred embodiment of the process according to the invention, the amount of catalyst discharge and thus the amount of fresh catalyst needed for supplementation is adjusted such that the content of nickel(0) complexes in the catalyst circulation does not fall below 0.05% by weight, more preferably not below 0.1% by weight, in particular not below 0.2% by weight, based in each case on the catalyst circulation and calculated in each case as metallic nickel(0), in order to ensure the activity of the hydrocyanation catalyst despite losses of nickel(0) complexes during the reaction in step (a) or during the distillation process in step (b) and (c), especially during the reaction in step (a).

In a further preferred embodiment of the process according to the invention, it is possible to transfer stream 1 which is obtained in process step (a) directly into process step (c) with exclusion of process step (b).

Stream 5 is subsequently transferred to a further distillation apparatus in process step (d). In this distillation apparatus, stream 5 is distilled to obtain a stream 7 which comprises 2-methyl-3-butenenitrile, and a stream 8 which comprises 3-pentenenitrile. Stream 7 is obtained at the top of the distillation apparatus, while stream 8 is obtained in the bottom of the distillation apparatus.

In a particularly preferred embodiment of the process according to the invention, stream 5 which is in some cases obtained as a gaseous side draw is transferred in gaseous form to the distillation apparatus of process step (d), and the pressure at the position of the feed point for stream 5 in the distillation apparatus of process step (d) is less than or equal to the pressure at the position of the side draw for stream 5 in the distillation apparatus of process step (c).

Not excluded from the scope of this description are process variants in which the pressure of stage (d) is selected freely and gas stream 5 is, if appropriate, compressed to a higher pressure than at the withdrawal point in (c) or liquefied by condensation and, if appropriate, conveyed with a pump, in order to be fed to stage (d).

Process step (d) of the process according to the invention may be carried out in any suitable apparatus known to those skilled in the art. Suitable apparatus for this distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in one apparatus.

The columns preferably contain structured packings. The structured packings preferably generate from 5 to 100, more preferably from 10 to 80, in particular from 15 to 50, theoretical plates.

The pressure in process step (d) is preferably from 0.001 to 100 bar, more preferably from 0.01 to 20 bar, in particular from 0.05 to 2 bar. The distillation is carried out in such a way that the temperature in the bottom of the distillation apparatus is preferably from 30 to 250° C., more preferably from 50 to 200° C., in particular from 60 to 180° C.

The distillation is carried out in such a way that the condensation temperature at the top of the distillation apparatus is preferably from −50 to 250° C., more preferably from 0 to 180° C., in particular from 15 to 160° C. In a particularly preferred embodiment of the process according to the invention, the aforementioned temperature ranges are maintained both at the top and in the bottom of the distillation apparatus.

In one embodiment of the process according to the invention, stream 7 which is obtained in process step (d) is fed to an isomerization according to DE-A-102 004 004 671.

In one embodiment of the process according to the invention, stream 7 which is obtained in process step (d) is recycled into process step (a) and/or into process step (b), and the reaction conditions in process step (a) or the residence time of the liquid phase in the bottom of process step (b) are selected in such a way that 2-methyl-3-butenenitrile is at least partly isomerized to trans-3-pentenenitrile.

In a further embodiment of the process according to the invention, stream 7 is obtained as a side draw stream in the distillation apparatus of process step (d), and the top product of this distillation column which is obtained is a stream which, in addition to 2-methyl-3-butenenitrile, also comprises substantially (Z)-2-methyl-2-butenenitrile and in some cases 1,3-butadiene and butene isomers, and also vinylcyclohexene and ethylidenecyclohexene. This embodiment is advantageous, since stream 7 is then richer in 2-methyl-3-butenenitrile than the top stream.

The content of trans-3-pentenenitrile in stream 7 is preferably from 0 to 50% by weight, more preferably from 100 ppm by weight to 20% by weight, in particular from 1 to 15% by weight. The content of 2-methyl-3-butenenitrile in stream 8 is preferably from 0 to 10% by weight, more preferably from 5 ppm by weight to 5% by weight, in particular from 50 ppm by weight to 1% by weight.

The process according to the invention enables the preparation of 3-pentenenitrile and 2-methyl-3-butenenitrile in an integrated process which, owing to the recycling, possible to a virtually full extent, of the 1,3-butadiene streams and the catalyst stream, has a high process yield for the feedstocks. The temperatures and pressure conditions needed for the distillative removal of 1,3-butadiene and pentenenitrile isomers from the catalyst streams can be selected in such a way that firstly the bottom evaporator temperatures when the process is practiced on the production scale with industrially achievable residence times are so low that they preferentially do not lead to catalyst damage, and that secondly the condensation of the top products of the particular distillation steps preferentially takes place at temperatures at which the heat removal on the production scale is possible with economically acceptable cost.

The present invention is illustrated in detail with reference to the working examples which follow.

In the examples, the following abbreviations are used:

| | |
|---|---|
| BD: | 1,3-butadiene |
| TBP: | tert-butylpyrocatechol |
| C2BU: | cis-2-butene |
| T3PN: | trans-3-pentenenitrile |
| 2M3BN: | 2-methyl-3-butenenitrile |
| Z2M2BN: | (Z)-2-methyl-2-butenenitrile |
| E2M2BN: | (E)-2-methyl-2-butenenitrile |
| MGN: | methylglutaronitrile and |
| ADN: | adiponitrile |
| HCN: | hydrogen cyanide |
| CAT: | catalyst |
| REG: | regeneration |

Example 1

Example 1 is illustrated with reference to FIG. 1.

In Example 1, a catalyst system based on nickel(0) complexes with a mixture of ligands is used for the hydrocyanation of BD. The ligand mixture for the hydrocyanation contains approx 60 mol % of tri(m/p-tolyl) phosphite and 40 mol % of the chelate phosphonite 1:

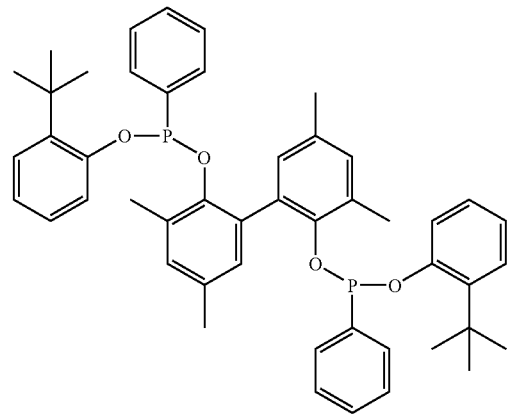

In a process step (a), the following streams are conducted into a loop reactor R1 of capacity 25 l which is equipped with a nozzle, impulse exchange tube, external pumped circulation and a heat exchanger disposed in the pumped circulation system to remove the energy of the reaction, and is heated to 357 K:

(1) 10 kg/h of liquid, unstabilized hydrogen cyanide freed of water by distillation;

(2) 22 kg/h of commercial BD containing 0.25% by weight of C2BU, which have been treated by contact with alumina in order to remove water and TBP stabilizer;

(3) 8 kg/h of recycled BD from column K1 of process step (b) (stream 2), so that the entire BD feed to reactor R1 which is obtained is a stream of 30 kg/h containing 90% by weight of BD, 5% by weight of C2BU and 5% by weight of 1-butene;

(4) 21 kg/h of nickel(0) catalyst solution, obtained as described below in this example, as stream 6a from column K2.

The stream 1 drawn off from reactor R1 (63 kg/h) contains a total of 11% by weight of BD and C2BU, corresponding to a conversion of 79% of BD, and also a total of 63% by weight of pentenenitriles, 31% by weight of T3PN, 29% by weight of 2M3BN, minor amounts of cis-3-pentenenitrile, trans-2-pentenenitrile, cis-2-pentenenitrile, 4-pentenenitrile and small amounts of Z2M2BN and E2M2BN, and also the catalyst constituents and catalyst degradation products and methylglutaronitrile.

In a process step (b), stream 1 is fed to a distillation column K1 which is operated with rectifying and stripping section, and is equipped with a failing-film evaporator and divided column bottom, and also column internals having structured packing which generate 10 theoretical plates. Column K1 is operated at the top with a direct condenser which consists of a column section equipped with structured packing and having a total collecting cup, pumped circulation and external heat exchanger. Column K1 is operated at an absolute pressure of 2.0 bar top pressure, top temperature 288 K and bottom draw temperature 363 K.

Via the top of column K1 is obtained stream 2 which, as described at the outset, is metered as a recycle stream into reactor R1. The reflux ratio at the top of column K1 is adjusted in such a way that stream 2 contains approx. 100 ppm of 2M3BN.

Via the bottom of column K1 are obtained 59 kg/h of a stream 3 which contains 2.9% by weight of BD, 4.6% by weight of C2BU, 67% by weight of pentenenitriles, and also additionally the catalyst constituents. C2BU is distinctly enriched in relation to BD compared to the feed.

In a process step (c), stream 3 is conducted into a distillation column K2 which is operated in stripping mode and is equipped with a falling-film evaporator, top condenser with postcondenser, and also column internals having structured packing which generate 10 theoretical plates. The column is operated at an absolute pressure of 150 mbar top pressure, top temperature 329 K and bottom draw temperature 373 K. The vapor stream of the column is partly condensed at 308 K and treated at 263 K with a postcondenser. The stream 4 thus depleted of 2M3BN and other pentenenitriles is compressed in a compressor V1 to an absolute pressure of 1.2 bar. The compressed gas stream is condensed at 279 K for the most part to obtain a stream 4a (5 kg/h), and a substream 4b (approx. 50 l (STP)/h, containing 44% by weight of C2BU) is disposed of in gaseous form. Stream 4a is recycled in liquid form into the reflux section of the divided column bottom of column K1.

In a gaseous side draw of column K2 is obtained stream 5 (40 kg/h) containing approx. 50 ppm of BD, 46% by weight of 2M3BN and 48% by weight of T3PN, and also, to a lesser extent, E2M2BN and Z2M2BN in addition to other pentenenitrile isomers. The position of the side draw is selected in such a way that the 2M3BN component in the stream 6 obtained via the bottom is depleted below the side draw in a stripping section in relation to T3PN.

Into column K2 are conducted 13 kg/h of a catalyst stream 10 containing a total of 73% by weight of pentenenitriles, 0.5% by weight of Ni(0), 18% by weight of ligand mixture and approx. 5% by weight of ADN.

Via the bottom of column K2 is obtained the catalyst stream 6 containing 0.5% by weight of Ni(0), approx. 100 ppm of 2M3BN and 35% by weight of residual pentenenitriles. Stream 6 is partly (stream 6a) recycled into reactor R1 (21 kg/h). Another portion (stream 6b: 5.4 kg/h) is fed to a regeneration (REG), described, for example, in DE-A-103 51 002, in order, after regeneration, to be used, for example, in Example 1 of the hydrocyanation of 3-pentenenitrile according to DE-A-102 004 004 683.

In a process step (d), stream 5 is conducted to a distillation column K3 which is equipped with circulation evaporator and top condenser, and also with a structured packing which generates 30 theoretical plates. Column K3 is operated at an absolute pressure of 180 mbar top pressure, top temperature 345 K and bottom draw temperature 363 K.

39 kg/h of a stream 9 are conducted into column K3, containing 54% by weight of T3PN, 23% by weight of 2M3BN and 16% by weight of Z2M2BN, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 1 of DE-A-102 004 004 671.

Via the top of column K3 are obtained 40 kg/h of a stream 7 containing 10% by weight of T3PN, 68% by weight of 2M3BN, 16% by weight of Z2M2BN, and also a total of 0.1% by weight of BD and C2BU. This stream may be fed to a process for isomerizing 2-methyl-3-butenenitrile to 3-pentenenitrile, as described in Example 1 of German patent application DE . . . with the title "Preparation of linear pentenenitrile" to BASF AG (B03/0436).

Via the bottom of column K3 are obtained 39 kg/h of stream 8 containing a total of 97% by weight of T3PN, C3PN and 4PN, and also approx. 100 ppm of 2M3BN and approx. 1% by weight of E2M2BN.

Example 1 shows how virtually full recovery of 1,3-butadiene is possible in a hydrocyanation process. In Example 1, the accumulation of cis-2-butene in the butadiene cycle is achieved firstly by the operation of column K1 with a stripping section and secondly by the discharge of a purge stream 4b at the evaporator V1, stream 4b (approx. 50 l (STP)/h) containing approx. 40% by volume of cis-2-butene.

The loss, found in Example 1, of 1,3-butadiene is small compared to Example 2, in which column K1 is operated without stripping section and the purge stream needed to limit the accumulations is drawn off as stream 2b at the top of column K1 (330 l (STP)/h) (with only 7% by weight of cis-2-butene and 92% by weight of 1,3-butadiene, which is to be attributed to economically significant losses).

Example 2

Figure 2:
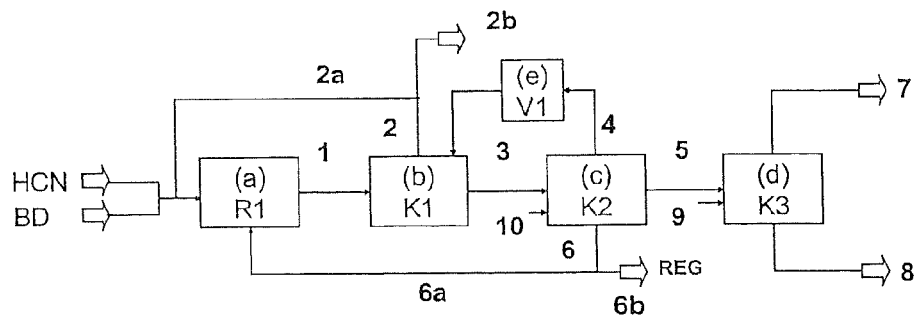

Example 2 is illustrated with reference to FIG. 2.

In Example 2, a catalyst system based on nickel(0) complexes with chelate phosphonite 1 as the ligand is used for the hydrocyanation:

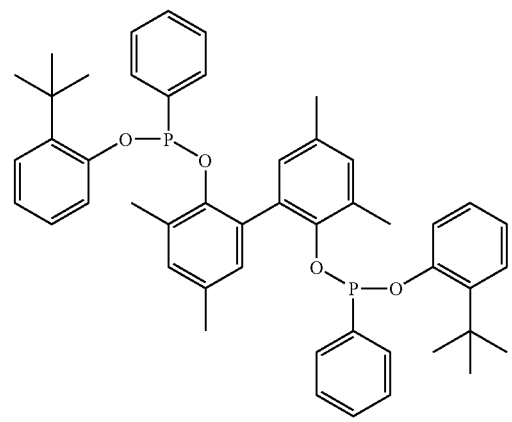

1

In a process step (a), the following streams are conducted into a loop reactor R1 of capacity 25 l which is equipped with a nozzle, impulse exchange tube, external pumped circulation and a heat exchanger disposed in the pumped circulation system to remove the energy of the reaction, and is heated to 357 K:

(1) 10 kg/h of liquid, unstabilized hydrogen cyanide freed of water by distillation;
(2) 22 kg/h of commercial BD containing 0.25% by weight of C2BU, which have been treated by contact with molecular sieve in order to remove water to concentrations of less than 10 ppm;
(3) 8 kg/h of recycled BD from K1 in process step (b) (stream 2a), so that the entire BD feed to reactor R1 which is obtained is a stream of 30 kg/h containing 90% by weight of BD, 8% by weight of C2BU and 2% by weight of 1-butene;
(4) 21 kg/h of nickel(0) catalyst solution, obtained as described below in this example, as stream 6a from column K2.

The stream 1 drawn off from reactor R1 (63 kg/h) contains a total of 13% by weight of BD and C2BU, corresponding to a conversion of 79% of BD, and also a total of 63% by weight of pentenenitriles, 31% by weight of T3PN, 29% by weight of 2M3BN, minor amounts of cis-3-pentenenitrile, trans-2-pentenenitrile, cis-2-pentenenitrile, 4-pentenenitrile and small amounts of Z2M2BN and E2M2BN, and also the catalyst constituents and catalyst degradation products and MGN.

In a process step (b), stream 1 is fed to a distillation column K1 which is operated with rectifying section and is equipped with a falling-film evaporator and divided column bottom, and also comprises column internals which generate 2 theoretical plates. Column K1 is operated at the top with a direct condenser which consists of a column section equipped with random packing and having a total collecting cup, pumped circulation and external heat exchanger. Column K1 is operated at an absolute pressure of 2.0 bar top pressure, top temperature 290 K and bottom draw temperature 363 K.

From the condenser circulation stream at the top of column K1, stream 2 is obtained which, as described at the outset, is metered partly as recycled stream 2a into reactor R1. The reflux ratio at the top of column K1 is adjusted in such a way that stream 2 contains approx. 100 ppm of 2M3BN.

The gaseous stream withdrawn from the top condenser of column K1 is a discharge stream 2b (approx. 330 l (STP)/h), containing 92% by weight of butadiene and 7% by weight of cis-2-butene, and also small amounts of 1-butene. The amount of discharge stream is such that the butadiene recycled stream 2a contains a total of approx. 10% by weight of 2-butene isomers and 1-butene.

Via the bottom of column K1 are obtained 59 kg/h of a stream 3 which contains 4.1% by weight of BD, 3.9% by weight of C2BU, 67% by weight of pentenenitriles and also additionally the catalyst constituents.

In a process step (c), stream 3 is conducted into a distillation column K2 which is operated in stripping mode and is equipped with falling-film evaporator, top condenser with postcondenser and also column internals having structured packing which generate 10 theoretical plates. The column is operated at an absolute pressure of 150 mbar top pressure, top temperature 354 K and bottom draw temperature 371 K.

The vapor stream of the column is partly condensed at 288 K and treated with a postcondenser at 263 K. The gaseous stream 4 (5 kg/h) thus depleted of 2M3BN and other pentenenitriles, containing 46% by weight of butadiene, 45% by weight of cis-2-butene and approx. 5% by weight of pentenenitrile isomers, is compressed in a compressor V1 to an absolute pressure of more than 2.0 bar in such a way that the pressure differential on the pressure side of the evaporator to the column K1 is sufficient to be able to conduct the compressed gas stream in gaseous form back into the column K1.

In a gaseous side draw of column K2 is obtained stream 5 (40 kg/h) containing approx. 50 ppm of BD, 46% by weight of 2M3BN and 48% by weight of T3PN, and also, to a smaller extent, E2M2BN and Z2M2BN in addition to other pentenenitrile isomers. The position of the side draw is selected in such a way that the 2M3BN component in the stream 6 obtained via the bottom is depleted in relation to T3PN in a stripping section below the side draw.

Into column K2 are conducted 13 kg/h of a catalyst stream 10 containing a total of 73% by weight of pentenenitriles, 0.5% by weight of Ni(0), 18% by weight of ligand mixture and approx. 5% by weight of ADN.

Via the bottom of column K2 is obtained the catalyst stream 6 (27 kg/h) containing 1.0% by weight of Ni(0), approx. 2000 ppm of 2M3BN and a total of 35% by weight of residual pentenenitriles. Stream 6 is partly (stream 6a) recycled into reactor R1 (21 kg/h). Another portion (stream 6b: 5.4 kg/h) may be fed to a regeneration (REG), described, for example, in DE-A-103 51 002.

In a process step (d), stream 5 is conducted to a distillation column K3 which is equipped with circulation evaporator and top condenser, and also with a structured packing which generates 30 theoretical plates. Column K3 is operated at an absolute pressure of 180 mbar top pressure, top temperature 345 K and bottom draw temperature 363 K.

39 kg/h of a stream 9 are conducted into column K3, containing 54% by weight of T3PN, 23% by weight of 2M3BN and 16% by weight of Z2M2BN, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 1 of DE-A-102 004 004 671.

Via the top of column K3 are obtained 40 kg/h of a stream 7 containing 10% by weight of T3PN, 68% by weight of 2M3BN, 16% by weight of Z2M2BN, and also a total of 0.1% by weight of BD and C2BU. This stream may be fed to a process for isomerizing 2-methyl-3-butenenitrile to 3-pentenenitrile, as described in Example 1 of DE-A-102 004 004 671.

Via the bottom of column K3 are obtained 39 kg/h of stream 8 containing a total of 97% by weight of T3PN, C3PN and 4PN, and also approx. 100 ppm of 2M3BN and approx. 1% by weight of E2M2BN.

In example 3, it can be shown that, in a method similar to example 2, distinctly lower REG losses have to be accepted in stream 2b when column K1 is equipped with a stripping section, since substantially cis-2-butene is discharged via column K2 to column K3 instead of 1,3-butadiene.

Example 3

Example 3 is likewise illustrated with reference to FIG. 2.

In Example 3, a catalyst system based on nickel(0) complexes with chelate phosphonite 1 as the ligand is used for the hydrocyanation:

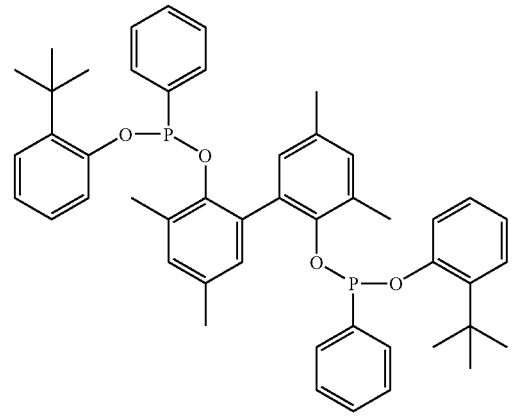

1

In a process step (a), the following streams are conducted into a loop reactor R1 of capacity 25 l which is equipped with a nozzle, impulse exchange tube, external pumped circulation and a heat exchanger disposed in the pumped circulation system to remove the energy of the reaction, and is heated to 357 K:

(5) 10 kg/h of liquid, unstabilized hydrogen cyanide freed of water by distillation;

(6) 22 kg/h of commercial BD containing 0.25% by weight of C2BU, which have been treated by contact with molecular sieve in order to remove water to concentrations of less than 10 ppm;

(7) 8 kg/h of recycled BD from K1 in process step (b) (stream 2a), so that the entire BD feed to reactor R1 which is obtained is a stream of 30 kg/h containing 90% by weight of BD, 4% by weight of C2BU and 6% by weight of 1-butene;

(8) 21 kg/h of nickel(0) catalyst solution, obtained as described below in this example, as stream 6a from column K2.

The stream 1 drawn off from reactor R1 (63 kg/h) contains a total of 13% by weight of BD and C2BU, corresponding to a conversion of 79% of BD, and also a total of 63% by weight of pentenenitriles, 31% by weight of T3PN, 29% by weight of 2M3BN, minor amounts of cis-3-pentenenitrile, trans-2-pentenenitrile, cis-2-pentenenitrile, 4-pentenenitrile and small amounts of Z2M2BN and E2M2BN, and also the catalyst constituents and catalyst degradation products and MGN.

In a process step (b), stream 1 is fed to a distillation column K1 which is operated with a rectifying and stripping section, and is equipped with a falling-film evaporator and divided column bottom, and also comprises column internals having structured packing which generate 10 theoretical plates. Column K1 is operated at the top with a direct condenser which consists of a column section equipped with structured packing and having a total collecting cup, pumped circulation and external heat exchanger. Column K1 is operated at an absolute pressure of 2.0 bar top pressure, top temperature 288 K and bottom draw temperature 363 K.

From the condenser circulation stream at the top of column K1, stream 2 is obtained which, as described at the outset, is metered partly as recycled stream 2a into reactor R1. The reflux ratio at the top of column K1 is adjusted in such a way that stream 2 contains approx. 100 ppm of 2M3BN.

The gaseous stream withdrawn from the top condenser of column K1 is a discharge stream 2b (approx. 55 l (STP)/h), containing 93% by weight of butadiene and 3% by weight of cis-2-butene, and also small amounts of 1-butene. The amount of discharge stream is such that the butadiene recycled stream 2a contains a total of approx. 10% by weight of 2-butene isomers and 1-butene.

Via the bottom of column K1 are obtained 59 kg/h of a stream 3 which contains 2.2% by weight of BD, 6.3% by weight of C2BU, 67% by weight of pentenenitriles and also additionally the catalyst constituents.

In a process step (c), stream 3 is conducted into a distillation column K2 which is operated in stripping mode and is equipped with falling-film evaporator, top condenser with postcondenser and also column internals having structured packing which generate 10 theoretical plates. The column is operated at an absolute pressure of 150 mbar top pressure, top temperature 354 K and bottom draw temperature 371 K.

The vapor stream of the column is partly condensed at 313 K and treated with a postcondenser at 263 K. Stream 4 (5 kg/h) thus depleted of 2M3BN and other pentenenitriles, containing in 23% by weight of butadiene, 66% by weight of cis-2-butene and approx. 5% by weight of pentenenitrile isomers, is compressed in a compressor V1 to an absolute pressure of more than 2.0 bar in such a way that the pressure differential on the pressure side of the evaporator to the column K1 is sufficient to be able to conduct the compressed gas stream in gaseous form back into the column K1.

In a gaseous side draw of column K2 is obtained stream 5 (40 kg/h) containing approx. 200 ppm of BD, 46% by weight of 2M3BN and 48% by weight of T3PN, and also, to a smaller extent, E2M2BN and Z2M2BN in addition to other pentenenitrile isomers. The position of the side draw is selected in such a way that the 2M3BN component in the stream 6 obtained via the bottom is depleted in relation to T3PN in a stripping section below the side draw.

Into column K2 are conducted 13 kg/h of a catalyst stream 10 containing a total of 73% by weight of pentenenitriles, 0.5% by weight of Ni(0), 18% by weight of ligand mixture and approx. 5% by weight of ADN.

Via the bottom of column K2 is obtained the catalyst stream 6 containing 1.0% by weight of Ni(0), approx. 2000 ppm of 2M3BN and a total of 35% by weight of residual pentenenitriles. Stream 6 is partly (stream 6a) recycled into reactor R1 (21 kg/h). Another portion (stream 6b: 5.4 kg/h) may be fed to a regeneration (REG), described, for example, in DE-A-103 51 002.

In a process step (d), stream 5 is conducted to a distillation column K3 which is equipped with circulation evaporator and top condenser, and also with a structured packing which generates 30 theoretical plates. Column K3 is operated at an absolute pressure of 180 mbar top pressure, top temperature 345 K and bottom draw temperature 363 K.

39 kg/h of a stream 9 are conducted into column K3, containing 54% by weight of T3PN, 23% by weight of 2M3BN and 16% by weight of Z2M2BN, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 1 of DE-A-102 004 004 671.

Via the top of column K3 are obtained 40 kg/h of a stream 7 containing 10% by weight of T3PN, 68% by weight of 2M3BN, 16% by weight of Z2M2BN, and also approx. 0.1% by weight of BD and approx. 1.5% by weight of C2BU. This stream may be fed to a process for isomerizing 2-methyl-3-butenenitrile to 3-pentenenitrile, as described in Example 1 of DE-A-102 004 004.

Via the bottom of column K3 are obtained 39 kg/h of stream 8 containing a total of 97% by weight of T3PN, C3PN and 4PN, and also approx. 100 ppm of 2M3BN and approx. 1% by weight of E2M2BN. Stream 8 can be used in a process for hydrocyanating 3-pentenenitrile to adiponitrile, as described in Example 1 of the hydrocyanation of 3-pentenenitrile according to DE-A-102 004 004 683.

Comparative Example

Figure 3:
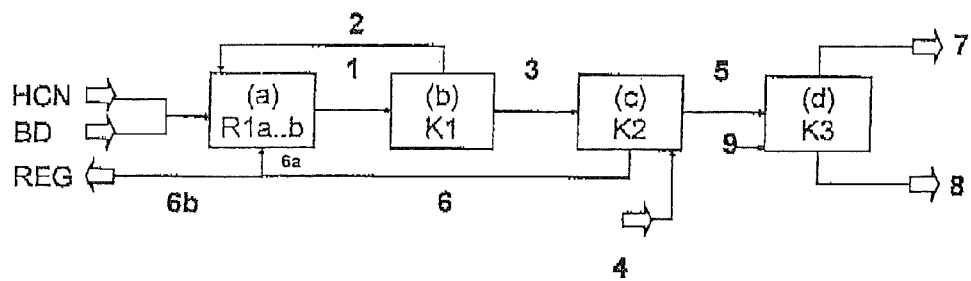

The comparative example is illustrated with reference to FIG. 3.

In the comparative example, a catalyst system based on nickel(0) complexes having chelate phosphite 2 as a ligand is used for the hydrocyanation:

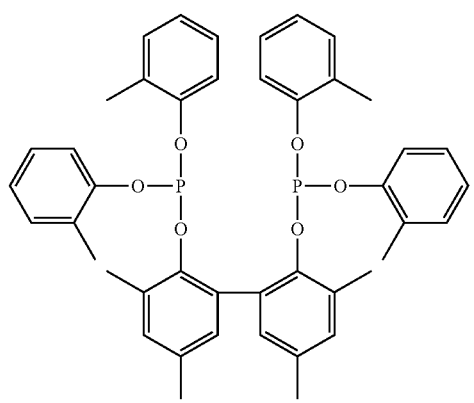

In a process step (a), the following streams are conducted into a system composed of two reactors R1a and R1b, each of capacity 12 l, and each of which is equipped with a nozzle, impulse exchange tube, external pumped circulation and a heat exchanger disposed in the pumped circulation system to remove the energy of reaction, and heated to 363 K:

(1) 6 kg/h of liquid, unstabilized hydrogen cyanide freed of water by distillation to R1a;
(2) 6 kg/h of liquid, unstabilized hydrogen cyanide freed of water by distillation to R1b;

(3) 25 kg/h of commercial BD to R1a, containing 0.25% by weight of C2BU, the BD having been treated by contact with alumina in order to remove water and TBP stabilizer;

(4) 2 kg/h of recycled BD from column K1 in process step (b) to R1a (stream 2), so that the entire BD feed to reactor R1 which is obtained is a stream of 27 kg/h containing 98% by weight of BD and a total of 2% by weight of C2BU and 1-butene;

(5) 14 kg/h of nickel(0) catalyst solution to R1a, obtained as described below in this example as stream 6a from column (K2).

The stream 1 drawn off from reactor R1b (54 kg/h) contains a total of 4% by weight of BD and C2BU, corresponding to a conversion of 94% of BD, and also a total of 74% by weight of pentenenitriles, of which 33% by weight is T3PN, 37% by weight is 2M3BN, minor amounts are cis-3-pentenenitrile, trans-2-pentenenitrile, cis-2-pentenenitrile, 4-pentenenitrile and small amounts are Z2M2BN and E2M2BN, and also the catalyst constituents and catalyst degradation products and methylglutaronitrile.

In a process step 2, stream 1 is fed to a distillation column K1 which is operated as a rectifying column and is equipped with a falling-film evaporator and also column internals having structured packing which generate 4 theoretical plates. Column K1 is operated at the top with a direct condenser which consists of a column section equipped with random packing and having total collecting cup, pumped circulation and external heat exchanger. Column K1 is operated at an absolute pressure of 0.8 bar top pressure, top temperature 263 K and bottom draw temperature 393 K.

Via the top of column K1 is obtained stream 2 which, as described at the outset, is metered into the reactor R1a as a recycle stream. The reflux ratio at the top of column K1 is adjusted in such a way that stream 2 contains 0.1% by weight of 2M3BN.

Via the bottom of column K1 are obtained 52 kg/h of a stream 3 which contains 0.3% by weight of BD, 0.1% by weight of C2BU, 76% by weight of pentenenitriles, and also additionally the catalyst constituents.

Within process step (c), stream 3 is conducted into a distillation column K2 which is operated in stripping mode and is equipped with a falling-film evaporator, top condenser with postcondenser, and also with column internals having structured packing which generate 4 theoretical plates. The column is operated at an absolute pressure of 70 mbar top pressure, top temperature 333 K and a bottom draw temperature 373 K.

At the gaseous top draw of column K2 is obtained stream 5 (40 kg/h) containing 0.4% by weight of BD, 54% by weight of 2M3BN and 42% by weight of T3PN, and also, to a lesser extent, E2M2BN and Z2M2BN in addition to other pentenenitrile isomers. 3 kg/h of a catalyst stream 4 are conducted into column K2, containing a total of 45% by weight of pentenenitriles, 1.5% by weight of Ni(0) and the chelate ligand, obtained, for example, by reacting nickel(0)(cyclooctadienyl)$_2$ complex with the chelate phosphite 2.

Via the bottom of column K2 is obtained the catalyst stream 6 containing 1.2% by weight of Ni(0), 0.3% by weight of 2M3BN and 17% by weight of residual pentenenitriles. Stream 6 is partly (stream 6a) recycled into reactor R1 (14 kg/h). Another portion (stream 6b: 3.8 kg/h) is fed to a regeneration (REG), described, for example, in DE-A-103 51 002, and may, after the regeneration, for example, be used in the hydrocyanation of 3-pentenenitrile or, if appropriate, be recycled into the hydrocyanation of butadiene according to the process according to the invention.

In a process step (d), stream 5 is conducted to a distillation column K3 which is equipped with circulation evaporator and top condenser, and also with a structured packing which generates 45 theoretical plates. Column K3 is operated at an absolute pressure of 1.0 bar top pressure, top temperature 395 K and bottom draw temperature 416 K.

24 kg/h of (stream 9) are fed into column K3, containing 70% by weight of T3PN, 14% by weight of 2M3BN and 7% by weight of Z2M2BN, and also small amounts of further pentenenitrile isomers. Stream 9 may be obtained, for example, as a recycled pentenenitrile stream from a process for isomerizing 2-methyl-3-butenenitrile to 3-pentenenitrile, as described in Example 2 of DE-A-102 004 004 671.

Via the top of column K3 are obtained 30 kg/h of a stream 7 containing 1% by weight of T3PN, 85% by weight of 2M3BN, 8% by weight of Z2M2BN, and also a total of 3% by weight of BD and C2BU. The reflux ratio of column K3 is adjusted in such a way that 1% by weight of 3-pentenenitrile is obtained overhead. This stream may, for example, be fed to a process for isomerizing 2-methyl-3-butenenitrile to 3-pentenenitrile, as described in Example 2 of DE-A-102 004 004 671.

Via the bottom of column K3 are obtained 38 kg/h of stream 8 containing a total of 97% by weight of T3PN, C3PN and 4PN, and also approx. 10 ppm of 2M3BN and approx. 2% by weight of E2M2BN and small amounts of methylglutaronitrile. Stream 8 may be fed to a process for hydrocyanating 3-pentenenitrile to adiponitrile, as described in Example 2 of DE-A-102 004 004 683.

The comparative example shows that either without the two-stage butadiene removal in the distillation stages K1 and K2 with recycling of the 1,3-butadiene without recompression or without the operation of the distillation stage K1 as a stripping column, distinctly less favorable temperature and pressure conditions have to be employed in stage K1 in order to achieve 1,3-butadiene loss rates which approach the values in example 1 to 3. The temperatures which are then necessary for sufficiently full 1,3-butadiene recycling in column K1 (120° C. in the comparative example instead of 90° C. in examples 1 to 3) lead, in the case of the thermally sensitive chelate ligands and the nickel complexes, irrespective of whether phosphite or phosphonites are used, to catalyst losses. The pressure of approx. 0.8 bar needed at bottom temperature 120° C. for depletion to approx. 0.5% by weight of 1,3-butadiene leads to very low temperatures of −10° C. at the top condenser in order to condense 1,3-butadiene and recycle it in liquid form into the reactors. The removal of heat of condensation at this temperature level of the comparative example is much more complicated than, for example, with cooling water, as is possible in example 1.

What is claimed is:

1. A process for preparing 3-pentenenitrile by hydrocyanating 1,3-butadiene, comprising by the following process steps:

(a) reacting 1,3-butadiene which comprises cis-2-butene with hydrogen cyanide over at least one catalyst to obtain a stream 1 which comprises 3-pentenenitrile, 2-methyl-3-butenenitrile, the at least one catalyst, 1,3-butadiene and residues of hydrogen cyanide which has yet to be converted, (b) distilling stream 1 in a distillation column K1 to obtain a stream 2 as the top product which comprises the predominant portion of the 1,3-butadiene from stream 1, and a stream 3 as the bottom product which comprises 3-pentenenitrile, the at least one catalyst, 2-methyl-3- butenenitrile and the remaining portion of the 1,3-butadiene from stream 1 which has not been removed in stream 2, (c) distilling stream 3 in a distillation column K2 to obtain a stream 4 as the top product which comprises 1,3-butadiene, a stream 5 which comprises 3-pentenenitrile and 2-methyl-3-butenenitrile at a side draw of the column, and a stream 6 as the bottom product which comprises the at least one catalyst, (d) distilling stream 5 to obtain a stream 7 as the top product which comprises 2-methyl-3-butenenitrile, and a stream 8 as the bottom product which comprises 3-pentenenitrile, the distillation column K1 used in process step (b) comprising at least one distillation column having a stripping section and/or the distillation column K2 used in process step (c) having distillative separation stages between the feed of stream 3 and the draw of stream 5 being disposed lower in the distillation column K2 than the feed of stream 3, and the at least one catalyst being Ni(O) which contains phosphorus ligands and/or free phosphorous ligands having the formula I:

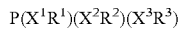

or the ligands having the formula II:

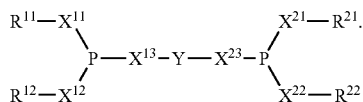

2. The process according to claim 1, wherein the distillation column K1 used in process step (b) has from 2 to 60 theoretical plates.

3. The process according to claim 1, wherein the stream 2 which is obtained in process step (b) and comprises 1,3-butadiene is recycled into process step (a), and/or the stream 4 which is obtained in process step (c) and comprises 1,3-butadiene is recycled into process step (a) and/or (b).

4. The process according to claim 1, wherein a substream 4b from the stream 4 obtained in process step (c) is discharged.

5. The process according to claim 1, wherein the distillation column K1 used in process step (b) has separation stages below the feed of stream 1 which enable enrichment of cis-2-butene relative to 1,3-butadiene in stream 3, and a substream 4b from the stream 4 obtained in process step (c) is discharged.

6. The process according to claim 4, wherein the discharge is in gaseous form.

7. The process according to claim 1 wherein, in the rectifying section of the distillation column K1 in process step (b), a stream is obtained in the boiling state at a side draw of the distillation column K1, condensed on a condenser by indirect heat removal to obtain a cooled stream and recycled to the top of the distillation column K1 of process step (b), and a stream 2' is drawn off before or after the condensation and the stream 2' is recycled into process step (a) instead of stream 2.

8. The process according to claim 1, wherein, in process step (c) before stream 4 is obtained, nitrile-containing compounds are depleted from the vapor stream by multistage condensation.

9. The process according to claim 1, wherein 1,3-butadiene required in addition to the recycled 1,3-butadiene is fed to process step (a).

10. The process according to claim 1, wherein 1,3-butadiene used in the process has no stabilizer, and a suitable selection of the pressure conditions keeps the condensation temperatures in the top region of the distillation column K1 of process step (b) less than 293 K in order to prevent polymerization of 1,3-butadiene, especially in order to limit the growth of popcorn polymer nuclei.

* * * * *